United States Patent [19]

Tarzia

[11] 4,072,689
[45] Feb. 7, 1978

[54] MONOAMINO 2,4,5-TRISUBSTITUTED OXAZOLES

[75] Inventor: Giorgio Tarzia, Rome, Italy

[73] Assignee: Gruppo Lepetit S.p.A., Milan, Italy

[21] Appl. No.: 641,410

[22] Filed: Dec. 17, 1975

Related U.S. Application Data

[63] Continuation of Ser. No. 334,928, Feb. 22, 1973, abandoned.

[51] Int. Cl.$^2$ .......................................... C07D 263/34
[52] U.S. Cl. ............................. 260/307 R; 424/272; 542/408; 542/418
[58] Field of Search ....................... 260/307 R, 240 G

[56] References Cited

PUBLICATIONS

"Bellsteins Handbuch der Org. Chemie.," Band XXVII, Syst. #4309, p. 324, (1937).
Zerilli et al., "Chem. Abst.," vol. 78, (1973), Abst. No. 92286j.
Sycheva et al., "Chem. Abst.," vol. 58, (1962), p. 1443h.
Finar, "Organic Chem.," vol. 1, p. 189, (1959), 3rd Ed.

*Primary Examiner*—Alton D. Rollins
*Assistant Examiner*—D. B. Springer
*Attorney, Agent, or Firm*—Daniel L. DeJoseph; C. Kenneth Bjork

[57] ABSTRACT

Pharmacologically active 2,4,5-trisubstituted oxazoles of the general formula

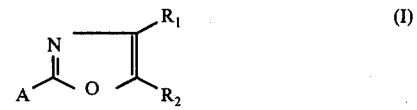

wherein A is cyclohexyl, thienyl or a group of the formula

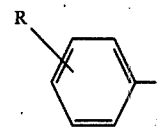

in which R represents one to three substituents each independently selected from the group consisting of hydrogen, lower alkyl, halo, halo-lower alkyl, lower alkoxy, nitro, cyano, amino, carbamoyl, acetamino or carboxy; one of the $R_1$ and $R_2$ groups is a lower alkyl group and the other is an amido group,

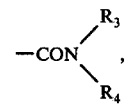

wherein $R_3$ is selected from the group consisting of hydrogen, lower alkyl, lower alkenyl, cycloalkyl, phenyl, substituted phenyl, phenyl-lower alkyl, hydroxy-lower alkyl, lower acyloxy-lower alkyl, hydroxy, amino, lower alkylideneamino, cycloalkylideneamino, benzylideneamino and $R_4$ is selected from hydrogen, lower alkyl, lower alkenyl, cycloalkyl, phenyl, substituted phenyl, phenyl-lower alkyl, hydroxy-lower alkyl, lower acyloxy-lower alkyl, and $R_3$ and $R_4$ taken together with the nitrogen atom may also form a 5- to 7-membered hetero ring which may contain one other hetero atom selected from N, O and S. The compounds have antiinflammatory activity.

5 Claims, No Drawings

MONOAMINO 2,4,5-TRISUBSTITUTED OXAZOLES

CROSS-REFERENCE TO RELATED APPLICATION

This is a continuation of application Ser. No. 334,928 Filed Feb. 22, 1973, now abandoned.

SUMMARY OF THE INVENTION

The present invention concerns pharmacologically active monoamido 2,4,5-trisubstituted oxazoles represented by the formula

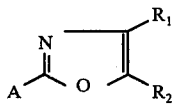

wherein A represents cyclohexyl, thienyl or a group of the formula

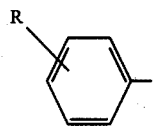

in which R represents one to three substituents each independently selected from the group consisting of hydrogen, lower alkyl, halo, halo-lower alkyl, lower alkoxy, nitro, cyano, amino, carbamoyl, acetamino or carboxy; one of the $R_1$ and $R_2$ groups represents a lower alkyl group and the other represents an amido group,

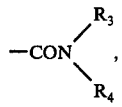

wherein $R_3$ is selected from the group consisting of hydrogen, lower alkyl, lower alkenyl, cycloalkyl, phenyl, substituted phenyl, phenyl-lower alkyl, hydroxy-lower alkyl, lower acyloxy-lower alkyl, hydroxy, amino, lower alkylideneamino, cycloalkylideneamino, benzylideneamino, substituted benzylideneamino, $R_4$ is selected from hydrogen, lower alkyl, lower alkenyl, cycloalkyl, phenyl, substituted phenyl, phenyl-lower alkyl, hydroxy-lower alkyl, lower acyloxy-lower alkyl, or $R_3$ and $R_4$ taken together with the nitrogen atom may also form a 5- to 7-membered hetero ring which may contain one other hetero atom selected from N, O and S. In the specification and claims, the terms "lower alkyl", "lower alkoxy", "lower alkylidene" and "lower alkenyl" designate straight or branched chain groups containing from 1 to 6 carbon atom alkyl, alkoxy and alkylidene and 3 to 6 carbon atom alkenyl groups; the term "cycloalkyl" designates 5 to 8 carbon atom cycloalkyl groups; "substituted phenyl" and "substituted benzylidene" designate phenyl and benzylidene having halo, lower alkyl or lower alkoxy substitution, respectively; the term "lower acyloxy" designates acetoxy, propionyloxy or butyryloxy; and the term "halo" designates fluoro, chloro or bromo.

A preferred group of compounds comprises those in which A represents cyclohexyl, thienyl or a group represented by the formula

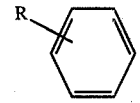

wherein R represents hydrogen or from one to three substituents selected from the group methyl, chloro, fluoro, methoxy or trifluoromethyl. It is obvious that when only one substituent is present, it can be in the ortho, meta or para position of the phenyl ring, and that when more than one substituent is present, all possible mutual positions may be occupied.

Another preferred group of compounds comprises those wherein $R_3$ represents hydrogen, lower alkyl, hydroxy, cyclopentyl, cyclohexyl, amino, isopropylideneamino or p-methylbenzylideneamino and $R_4$ represents hydrogen or lower alkyl.

A further preferred group of compounds comprises those in which $R_1$ or $R_2$ are lower alkyl groups containing from 1 to 3 carbon atoms.

The compounds of the present invention exhibit anti-inflammatory activity, and, in some cases, they also have analgetic properties. Moreover, they have a very low toxicity.

The general method for preparing the compounds of this invention comprises reacting a compound of the formula

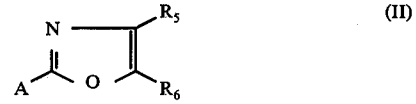

wherein A has the meaning given above and one of the $R_5$ or $R_6$ groups is lower alkyl and the other a group of the formula

(III) in which $R_7$ is a halo or a lower alkoxy group, with an amine of the formula

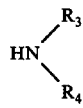

(IV) wherein $R_3$ and $R_4$ have the meanings given above. The presence of an inert organic solvent is usually advantageous and is preferred. When an oxazole of the Formula (II) wherein $R_5$ or $R_6$ represents the group

and $R_7$ is a halo group is employed as the starting material, the presence of a tertiary amine or an excess of the amine of Formula (IV) is required to block the hydrogen halide which is formed during the reaction. In the preferred mode of carrying out the reaction in the presence of an inert organic solvent, for example, if in the compound of Formula (III) $R_7$ is a lower alkoxy group, the preferred solvent is selected from the lower alkanols or an excess of the amine of Formula (IV). On the other hand, when $R_7$ represents a halo group, the solvent is generally an inert organic liquid, such as, for example benzene, toluene, a chlorinated hydrocarbon, dioxane, and tetrahydrofuran. The temperature at which the reaction is carried out is not critical and is generally in the range between room temperature and the boiling temperature of the solvent. The compounds of the invention wherein $R_3$ represents a lower alkylideneamino, a cycloalkylidene or a benzylideneamino group are more conveniently prepared from the corresponding derivatives when the foregoing radical is an amino group through a condensation with a predetermined aldehyde or ketone by conventional methods. The compounds wherein $R_3$ or $R_4$ are lower acyloxy-lower alkyl groups are prepared from the corresponding hydroxy compounds by usual acylation procedures.

The compounds of the invention are generally soluble in organic media such as acetic acid, dioxane, dimethylformamide and dimethylsulfoxide. The compounds in which $R_3$ and $R_4$ are hydrogen are fairly soluble in lower alkanols or chloroform and generally have a very low solubility in water. Suitable solvents for the crystallization of these products are mixtures of water and dimethylformamide; water and lower alkanols; lower alkanols; and in some cases water and hexane, depending on the nature of the substituents of position 4 or 5.

DESCRIPTION OF SOME PREFERRED EMBODIMENTS

The following non-limitative examples describe in detail enabling representative embodiments and the best modes contemplated by the inventor for carrying out the inventions. Temperature is given in centigrade degrees.

EXAMPLE 1

5-Carbamoyl-4-methyl-2-phenyloxazole

150 Ml. (2.5 mole) of concentrated ammonium hydroxide is added dropwise to a solution of 10 g. (0.0434 mole) of 5-carbethoxy-2-phenyl-4-methyloxazole in 150 ml. of 95% ethanol. The mixture is stirred three days at room temperature, then it is concentrated to 50 ml. by evaporating the ethanol and chilled. The precipitated product is filtered, washed, dried over sodium sulfate and recrystallized from methanol; yield 3.7 g. of the title compound; m.p. 187°–190°.

EXAMPLE 2

4-Carbamoyl-5-methyl-2-phenyloxazole 9.4 Grams (0.0425 mole) of 5-methyl-2-phenyl-4-oxazolecarboxylic acid chloride is added in small portions to 200 ml. (3.33 mole) of concentrated ammonium hydroxide. The mixture is vigorously stirred and the temperature is maintained at about 0° during the addition step. After the addition, the temperature is allowed to rise to room temperature and the mixture is left standing overnight. The solid which forms is collected by filtration, washed with water, dried and recrystallized from methanol. 6.35 Grams of the title product is obtained; m.p. 154°–157° (from methanol).

EXAMPLES 3–5

Pursuant to the procedure described in Example 1, the following compounds are prepared:
(3) 4-Carbamoyl-5-methyl-2-(2-thienyl)oxazole, by reacting 4-carbethoxy-5-methyl-2-(2-thienyl)oxazole with ammonium hydroxide. Yield 66%, m.p. 159°–161° (from methanol).
(4) 4-Cyclohexylcarbamoyl-5-methyl-2-(2-thienyl)-oxazole, by reacting 4-carbethoxy-5-methyl-2-(2-thienyl)-oxazole with cyclohexylamine. Yield 61%, m.p. 128°–129° (from diethyl ether).
(5) 4-Carbamoyl-5-methyl-2-(p-fluorophenyl)-oxazole, by reacting 4-carbethoxy-5-methyl-2-(p-fluorophenyl)oxazole with ammonium hydroxide. Yield 70%, m.p. 177°–180° (from diethyl ether).

Pursuant to the procedure described in Example 2, the following compounds are prepared:
(6) 4-Carbamoyl-2-(p-chlorophenyl)-5-methyloxazole, by reacting 2-(p-chlorophenyl)-5-methyl-4-oxazolecarboxylic acid chloride with ammonium hydroxide. Yield 82%, m.p. 199°–201° (from methanol).
(7) 2-(p-Chlorophenyl)-4-ethylcarbamoyl-5-methyloxazole, by reacting 2-(p-chlorophenyl)-5-methyl-4-oxazolecarboxylic acid chloride with ethylamine. Yield 77%, m.p. 98°–100° (from diethyl ether).
(8) 2-(p-Chlorophenyl)-4-cyclohexylcarbamoyl-5-methyloxazole, by reacting 2-(p-chlorophenyl)-5-methyl-4-oxazolecarboxylic acid chloride with cyclohexylamine. Yield 84%, m.p. 150°–152° (from diethyl ether).
(9) 4-Carbamoyl-5-methyl-2-(p-tolyl)oxazole, by reacting 5-methyl-2-(p-tolyl)-4-oxazolecarboxylic acid chloride with ammonium hydroxide. Yield 75%, m.p. 169°–170° (from methanol).
(10) 4-Ethylcarbamoyl-5-methyl-2-(p-tolyl)oxazole, by reacting 5-methyl-2-(p-tolyl)-4-oxazolecarboxylic acid chloride with ethylamine. Yield 80%, m.p. 99°–101° (from diethyl ether).
(11) 4-Cyclohexylcarbamoyl-5-methyl-2-(p-tolyl)oxazole, by reacting 5-methyl-2-(p-tolyl)-4-oxazolecarboxylic acid chloride with cyclohexylamine. Yield 75%, m.p. 146°–149° (from diethyl ether).
(12) 4-Carbamoyl-2-cyclohexyl-5-methyloxazole, by reacting 2-cyclohexyl-5-methyl-4-oxazolecarboxylic acid chloride with ammonium hydroxide. Yield 72%, m.p. 131°–133° (from diethyl ether).
(13) 2-Cyclohexyl-4-ethylcarbamoyl-5-methyloxazole, by reacting 2-cyclohexyl-5-methyl-4-oxazolecarboxylic acid chloride with ethylamine. Yield 87%, b.p. 160°/0.6 mm Hg.
(14) 2-Cyclohexyl-4-cyclohexylcarbamoyl-5-methyloxazole, by reacting 2-cyclohexyl-5-methyl-4-oxazolecarboxylic acid chloride with cyclohexylamine. Yield 82%, m.p. 52°–54° (from diethyl ether).
(15) 4-Carbamoyl-2-(o-fluorophenyl)-5-methyloxazole, by reacting 2-(o-fluorophenyl)-5-methyl-4-oxazolecarboxylic acid chloride with ammonium hydroxide. Yield 78%, m.p. 162°–164° (from methanol).
(16) 4-Ethylcarbamoyl-2-(o-fluorophenyl)-5-methyloxazole, by reacting 2-(o-fluorophenyl)-5-methyl-4-oxazolecarboxylic acid chloride with ethylamine. Yield 86%, m.p. 53°–55° (from diethyl ether).
(17) 4-Cyclohexylcarbamoyl-2-(o-fluorophenyl)-5-methyloxazole, by reacting 2-(o-fluorophenyl)-5-methyl-4-oxazolecarboxylic acid chloride with cyclohexylamine. Yield 78%, m.p. 69°–72°(from diethyl ether).

(18) 5-Cyclohexylcarbamoyl-4-methyl-2-phenyloxazole, by reacting 4-methyl-2-phenyl-5-oxazolecarboxylic acid chloride with cyclohexylamine. Yield 81%, m.p. 144°–146° (from diethyl ether).

Typical compounds which are prepared pursuant to procedures hereinbefore described in the examples are listed below, 5-Methyl-2-phenyl-4-oxazolecarboxylic acid hydrazide
5-Methyl-2-phenyl-4-pentylcarbamoyl-oxazole
5-Methyl-2-phenyl-4-n-propyl-oxazole
4-Benzylcarbamoyl-5-methyl-2-phenyl-oxazole
4-Allylcarbamoyl-5-methyl-2-phenyl-oxazole
4-(2-Hydroxyethylcarbamoyl)-5-methyl-2-phenyl-oxazole
4-(3-Hydroxypropylcarbamoyl)-5-methyl-2-phenyl-oxazole
4-Isopropylcarbamoyl-5-methyl-2-(p-tolyl)oxazole
4-Isobutylcarbamoyl-5-methyl-2-phenyl-oxazole
4-Cyclohexylcarbamoyl-5-methyl-2-phenyl-oxazole
5-Methyl-4-morpholinocarbonyl-2-phenyl-oxazole
4-Carbamoyl-5-methyl-2-(3,4,5-trimethoxyphenyl)oxazole
4-Carbamoyl-5-methyl-2-(m-tolyl)oxazole
4-Carbamoyl-5-methyl-2-(o-tolyl)oxazole
4-Carbamoyl-5-methyl-2-(m-trifluoromethylphenyl)oxazole
4-Carbamoyl-2-(m-chlorophenyl)-5-methyl-oxazole
4-Cyclohexylcarbamoyl-2-(p-fluorophenyl)-5-methyl-oxazole
4-Carbamoyl-2-(o-chlorophenyl)-5-methyloxazole
4-Carbamoyl-5-ethyl-2-(p-tert. butylphenyl)oxazole
4-Carbamoyl-5-ethyl-2-(m-trifluoromethylphenyl)oxazole
4-Cyclohexylcarbamoyl-2-(m-methoxyphenyl)-5-propyl-oxazole
2-(m-Chlorophenyl)-4-(2-hydroxypropylcarbamoyl)-5-isopropyloxazole
4-(2-Acetoxyethylcarbamoyl)-5-methyl-2-phenyl-oxazole
4-(2-Acetoxypropylcarbamoyl)-5-methyl-2-phenyl-oxazole
4-Dipropylcarbamoyl-5-methyl-2-phenyl-oxazole
4-Dicyclohexylcarbamoyl-5-ethyl-2-(p-methoxyphenyl)-oxazole
4-Diethylcarbamoyl-5-(3,5-dimethylphenyl)-5-propyl-oxazole
5-Methyl-2-phenyl-4-oxazolecarbohydroxamic acid
5-Methyl-2-(p-tolyl)-4-oxazolecarbohydroxamic acid
2-(p-Chlorophenyl)-5-methyl-4-oxazolecarbohydroxamic acid
5-Ethyl-2-(p-methoxyphenyl)-4-oxazolecarbohydroxamic acid
2-(p-Fluorophenyl)-5-methyl-4-oxazolecarbohydroxamic acid
5-Methyl-2-phenyl-4-oxazolecarboxylic acid isopropylidenhydrazide
5-Methyl-2-phenyl-4-oxazolecarboxylic acid 4-methyl-benzylidene hydrazide
2-Phenyl-5-propyl-4-oxazolecarboxylic acid cyclohexylidene hydrazide
4-Methyl-2-phenyl-5-oxazolecarboxylic acid hydrazide
4-Methyl-2-phenyl-5-pentylcarbamoyl-oxazole
5-Benzylcarbamoyl-4-methyl-2-(p-methoxyphenyl)oxazole
5-Allylcarbamoyl-4-methyl-2-phenyl-oxazole
5-(3-Hydroxypropylcarbamoyl)-4-methyl-2-phenyloxazole
5-Isobutylcarbamoyl-4-methyl-2-phenyl-oxazole
5-Cyclohexylcarbamoyl-4-ethyl-2-(m-methoxyphenyl)oxazole
5-Carbamoyl-4-methyl-2-(m-trifluoromethylphenyl)oxazole
5-Carbamoyl-2-(o-fluorophenyl)-4-methyl-oxazole
5-Cyclohexylcarbamoyl-2-(p-fluorophenyl)-4-methyloxazole
5-Carbamoyl-2-(o-chlorophenyl)-4-methyl-oxazole
4-Methyl-5-(4-methyl-1-piperazinylcarbonyl)-2-phenyloxazole
5-Carbamoyl-4-ethyl-2-(p-tert. butylphenyl)oxazole
5-Carbamoyl-4-ethyl-2-(m-trifluoromethylphenyl)oxazole
5-Cyclohexylcarbamoyl-2-(m-methoxyphenyl)-4-propyl-oxazole
5-(2-Acetoxypropylcarbamoyl)-4-methyl-2-phenyl-oxazole
5-Dicyclohexylcarbamoyl-4-ethyl-2-(p-methoxyphenyl)-oxazole
4-Methyl-2-phenyl-5-oxazolecarbohydroxamic acid
4-Methyl-2-(p-tolyl)-5-oxazolecarbohydroxamic acid
2-(p-Chlorophenyl)-4-methyl-5-oxazolecarbohydroxamic acid
4-Ethyl-2-(p-methoxyphenyl)-5-oxazolecarbohydroxamic acid
2-Phenyl-4-propyl-5-oxazolecarboxylic acid isopropylidene hydrazide
4-Methyl-2-phenyl-5-oxazolecarboxylic acid 4-methyl-benzylidene hydrazide
2-Phenyl-4-propyl-5-oxazolecarboxylic acid cyclohexylidene hydrazide
4-Carbamoyl-5-methyl-2-(m-nitrophenyl)oxazole
4-Carbamoyl-5-methyl-2-(p-nitrophenyl)oxazole
4-Carbamoyl-2-(p-cyanophenyl)-5-isopropyl-oxazole
5-Carbamoyl-2-(p-carboxyphenyl)-4-ethyl-oxazole
4-Carbamoyl-2-(p-carboxyphenyl)-5-ethyl-oxazole
2-(p-Carbamoylphenyl)-4-carbamoyl-5-methyl-oxazole
2-(o-Aminophenyl)-4-carbamoyl-5-ethyl-oxazole
2-(m-Aminophenyl)-4-carbamyl-5-ethyl-oxazole
2-(m-Aminophenyl)-5-carbamoyl-4-ethyl-oxazole
2-(p-Aminophenyl)-5-carbamoyl-4-methyl-oxazole
2-(o-Acetaminophenyl)-4-carbamoyl-5-methyl-oxazole
2-(m-Acetaminophenyl)-4-carbamoyl-5-methyl-oxazole
2-(p-Acetaminophenyl)-4-carbamoyl-5-methyl-oxazole
2-(o-Acetaminophenyl)-5-carbamoyl-4-oxazole
4-Carbamoyl-5-methyl-2-(m-sulfamoylphenyl)oxazole
4-Carbamoyl-5-methyl-2-(p-sulfamoylphenyl)oxazole The compounds of the invention have antiinflammatory activity. Doses varying from one-twentieth to one-fifth of the $LD_{50}$ values p.o. are highly effective in the art-accepted carrageenin-induced edema test in rats. The compounds are orally administered at dosages varying from 10 to 200 mg/kg. and the observed percent decreases of the induced edema are between about 30 and about 65. The acute toxicity of these compounds is ordinarily very low, almost always being higher than 1000 mg/kg. Moreover the compounds of this invention are much less ulcerogenic than other known and wisely used anti-inflammatories, such as, for example, phenylbutazone.

The following table presents results representative of those obtainable with the compounds of this invention.

TABLE

| Compound of Example | LD$_{50}$ mg/kg p.o. mice | Dose, mg/kg p.o., mice | Percent inhibition of carrageenin induced edema |
|---|---|---|---|
| 1 | >1000 | 50 | 30 |
|  |  | 100 | 43 |
|  |  | 200 | 64 |
| 2 | >1000 | 50 | 29 |
|  |  | 100 | 42 |
|  |  | 200 | 53 |

The 4- and 5-carbalkoxyoxazole starting materials were prepared following the methods described by Chiaki Tanaka and Norio Saito in Yakugaku Zasshi 82, 136, 1962 (Chem. Abs. 58, 3407 d, 1962 and Chem. Abs. 58, 3407 h, 1962). From these carbalkoxyoxazole starting materials the corresponding acyl halides were obtained by means of usual procedures, i.e., by hydrolysis of the carbalkoxy group and subsequent reaction with a thionyl or phosphorus halide.

The melting points of the oxazolecarboxylic acid derivative starting materials of Examples 1-14 are given hereinbelow.

| STARTING MATERIAL OF EXAMPLE | M.P. (SOLVENT OF RECRYSTALLIZATION) |
|---|---|
| 1 | 52–54° (Light petroleum) |
| 2 | 133–135° (diethyl ether/hexane) |
| 3–4 | 91–93° (hexane) |
| 5 | 70–73° (hexane) |
| 6–7–8 | 141–144° (diethyl ether/hexane) |
| 9–10–11 | 118–121° (diethyl ether/hexane) |
| 12–13–14 | 159–62° (diethyl ether/hexane) |
| 15–16–17 | decomposes; use immediately after preparation |
| 18 | 82–84° (diethyl ether/hexane) |

What is claimed is:
1. 5-Carbamoyl-4-methyl-2-phenyloxazole, 4-carbamoyl-5-methyl-2-phenyloxazole, 4-cyclohexylcarbamoyl-5-methyl-2-(p-tolyl)oxazole or 4-carbamoyl-2-(o-fluorophenyl)-5-methyloxazole.
2. The compound of claim 1 which is 5-carbamoyl-4-methyl-2-phenyloxazole.
3. The compound of claim 1 which is 4-carbamoyl-5-methyl-2-phenyloxazole.
4. The compound of claim 1 which is 4-cyclohexylcarbamoyl-5-methyl-2-(p-tolyl)oxazole.
5. The compound of claim 1 which is 4-carbamoyl-2-(o-fluorophenyl)-5-methyloxazole.

UNITED STATES PATENT AND TRADEMARK OFFICE
CERTIFICATE OF CORRECTION

PATENT NO. : 4,072,689

DATED : February 7, 1978

INVENTOR(S) : Giorgio Tarzia, Rome, Italy

It is certified that error appears in the above-identified patent and that said Letters Patent are hereby corrected as shown below:

On first page under PUBLICATIONS, "Bellsteins Handbuch der Org. Chemie.," Band XXVII," should read -- "Beilsteins Handbuch der Org. Chemie.," Band XXVII, --;

On first page under ABSTRACT, fourth paragraph, 9th line, "and $R_3$" should read -- or $R_3$ --;

Column 3, line 30 "and hexane" should read --or hexane--;

Column 6, line 43 "2-(mAminophenyl)" should read -- 2-(m-Aminophenyl) --;

Column 6, line 49 "-4-oxazole" should read -- -4-methyl-oxazole --;

Column 8, line 7 of TABLE "159-62°" should read -- 159-162° --.

Signed and Sealed this

Seventeenth Day of October 1978

[SEAL]

Attest:

RUTH C. MASON
Attesting Officer

DONALD W. BANNER
Commissioner of Patents and Trademarks